United States Patent [19]

Harris et al.

[11] 4,278,653

[45] Jul. 14, 1981

[54] METHODS AND KITS FOR DOUBLE ANTIBODY IMMUNOASSAY PROVIDING A COLORED PELLET FOR EASY VISUALIZATION

[75] Inventors: S. Richard Harris, Needham; Darlene K. Bonci, W. Boylston, both of Mass.

[73] Assignee: New England Nuclear Corporation, Boston, Mass.

[21] Appl. No.: 8,267

[22] Filed: Feb. 1, 1979

[51] Int. Cl.$^3$ ...................... G01N 33/56; G01N 33/78
[52] U.S. Cl. ........................................ 424/1; 23/230 B; 23/230.3; 23/915; 23/920; 23/923; 422/61
[58] Field of Search ................... 23/230 B, 915, 920, 23/923, 230.3; 424/1, 12; 422/61

[56] References Cited

U.S. PATENT DOCUMENTS

| | | | |
|---|---|---|---|
| 3,716,632 | 2/1973 | Rader et al. | 23/230 B X |
| 3,853,987 | 12/1974 | Dreyer | 23/230 B X |
| 3,879,262 | 4/1975 | Wilhelmus et al. | 424/12 X |
| 3,985,867 | 10/1976 | Redshaw | 23/230 B X |
| 4,108,974 | 8/1978 | Wegfahrt et al. | 23/230 B X |

OTHER PUBLICATIONS

Desbuquois et al., "Use of Polyethylene Glycol to Separate Free and Antibody-Bound Peptide Hormones in Radioimmunoassays", J. Clin. Endocr., 33, pp. 732–738, (1971).
Yalow et al., "General Principles of Radioimmunoassay", in *Radioisotopes in Medicine: In Vitro Studies*, edit. by Hayes et al. pp. 7–41, (Jun. 1968).
Hellsing, "Enhancing Effects of Nonionic Polymers on Immunochemical Reactions", Chapter 3 of Automated Analysis-Part 1", in Clinical & Biochemical Analysis, vol. 7, pp. 67–112.
Creighton et al., "Detection of Antibodies and Soluble Antigen-Antibody Complexes by Precipitation with Polyethylene Glycol", J. Immuno. vol. III, No. 4, pp. 1219–1227, 10-1973.
Harington et al., "Polymer-Induced Precipitation of Antigen-Antibody Complexes: 'Precipiplex' Reactions", *Immunochemistry*, vol. 8, pp. 413–421, (1971).
Aach et al., "Detection of Australian Antigen by Radioimmunoassay", *Proc. Nat. Acad. Sci. USA*, vol. 68, No. 5, pp. 1056–1060, (May 1971).

*Primary Examiner*—Arnold Turk
*Attorney, Agent, or Firm*—Sewall P. Bronstein; George W. Neuner

[57] ABSTRACT

Methods and kits for performing a double antibody immunoassay are described. The immunoassay comprises:

reacting an antigen and a labelled version of said antigen with a first antibody against said antigen and said first antibody with a second antibody against said first antibody to precipitate a complex of said antigen, said first antibody and said second antibody, and precipitating a colored protein to form a precipitate comprised of said complex and colored protein.

In a preferred embodiment, the first and second antibodies can be prereacted to simplify the assay procedure.

52 Claims, No Drawings

METHODS AND KITS FOR DOUBLE ANTIBODY IMMUNOASSAY PROVIDING A COLORED PELLET FOR EASY VISUALIZATION

FIELD OF THE INVENTION

This invention relates to immunoassays of the kind in which an unknown amount of an antigen to be assayed and a standard amount of a labelled version of the antigen compete for reaction with a standard amount of an antibody. This invention can be used in the medical field for assaying drugs, hormones, peptides, and other substances.

In particular, this invention relates to methods for double antibody immunoassay in which a colored pellet is provided and to immunoassay kits comprising ingredients to practice such methods for immunoassay. Generally, the labelled version of the antigen is a radioactive-labelled compound; however other forms of labelling could be employed.

BACKGROUND OF THE INVENTION

In the double antibody immunoassay reaction an amount of labelled antigen and unlabelled antigen compete to react with an amount of antibody that is insufficient to bind all of the labelled and unlabelled antigen. An equilibrium is set up in which the amount of bound labelled antigen and free labelled antigen is controlled by the amount of unlabelled antigen present in the assay. The amount of unlabelled antigen can then be determined by measuring the amount of free or bound labelled antigen and a calibration curve generated by the use of standard preparations of unlabelled antigen.

The technique is described, with examples, in a Review Paper by R. S. Yalow and S. A. Berson in IAEA-SM-124/106, pages 455-481.

Various techniques are known for separating the bound from the free antigen. One technique involves attaching the antibody to an insoluble carrier such as described in U.S. Pat. No. 3,853,987.

Another technique for separating the bound from the free antigen involves the precipitation of the antigen-antibody complex out of solution by the addition of a second antibody directed against the serum or gamma globulin of the animal species used to generate the first antibody. This second antibody may be added either in solution or adsorbed or covalently bound to an insoluble carrier such as cellulose.

Both types of second antibody addition suffer from disadvantages. Addition of the second antibody adsorbed on a solid carrier gives rise to difficulties in ensuring that homogeneous slurry additions are made, and slower equilibrium attainment is generally found. Additionally, quite a large amount of second antibody is generally required and relatively complex chemical manipulations (to prepare the insolubilized material) are needed, resulting in greatly increased cost.

Addition of the second antibody as a solution avoids most of these problems; but it can result in the formation of only a minute quantity of whitish or translucent precipitate which may be virtually invisible after centrifuging. Inability to see the solid deposit in the assay tube makes it difficult for an operator, particularly an inexperienced one, to remove the supernatant liquid before measurement of the activity of the deposit.

One solution to this problem which has been used is to add extra carrier serum, (serum from a nonimmunized animal of the same species in which the primary antiserum is made), while still using an increased amount of the second antibody, so as to increase the physical bulk of the precipitate. This solution, however, requires considerable second antibody and often results in the same translucent pellet that is difficult to handle because of poor visualization.

Another solution described in U.S. Pat. No. 3,985,867 involves coloring the second antibody so that the precipitate formed is colored and is thus more clearly visible. This procedure, however, involves a complex process for preparing the dyed antibody in which the second antibody must be coupled to a solid phase bearing the first antibody for dyeing, washed, and then separated from the solid phase. Assay procedures using the dyed second antibody require the same large volume of the antibody as do conventional assays, as well as nonimmune carrier serum, in order to obtain a pellet large enough to be visible. Further, binding a dye to the antibodies can inhibit their efficiency in the immunoassay.

SUMMARY OF THE INVENTION

The present invention provides, among other things, a relatively simple means for visualizing the pellet in a double antibody immunoassay. In addition, the present invention allows the formation of a pellet the size of which is relatively insensitive to the amount of second antibody and carrier present in the assay. Therefore, carrier can be eliminated and less second antibody can be used, greatly lowering cost per assay.

Accordingly, the present invention provides a method for performing an immunoassay, the method comprising:

reacting an antigen and a labelled version of said antigen with a first antibody for said antigen and said first antibody with a second antibody for said first antibody to precipitate a complex of said antigen, said first antibody and said second antibody, and precipitating a colored protein to form a precipitate comprised of said complex and colored protein.

The invention also provides an immunoassay kit comprising:

1. a predetermined amount of a labelled version of the antigen to be assayed.
2. a predetermined amount of a first antibody to react with the antigen to be assayed to form a first antibody-antigen complex;
3. a predetermined amount of a second antibody to react with the first antibody-antigen complex to form a precipitate;
4. a predetermined amount of a colored protein; and
5. a predetermined amount of a precipitating agent to effect the coprecipitation of at least some of the colored protein.

The term "complex" as used herein refers to the reaction product of an antigen and an antibody or a first antibody and a second antibody to the first antibody (i.e. an anti-antibody).

DETAILED DESCRIPTION OF THE INVENTION

In accord with the present invention, a method for double antibody immunoassay is provided that yields a colored pellet for easy visualization and kits for performing such an immunoassay. The invention is applicable to any antigen that can be assayed by the double antibody immunoassay technique. Exemplary classes of antigen include, for instance, drugs, steroids, hormones and peptides. Examples of such antigens include, for instance, gentamicin, tobramycin, theophylline, digoxin, hydrocortisone, etc. Further examples of antigens are given in the article by Yalow and Berson, mentioned above, which is hereby incorporated by reference.

Any suitable means for labelling the antigen can be used. Labelling by means of a radioactive isotope is presently preferred.

The antibodies are prepared by conventional techniques. For instance, the first antibody can be induced by introducing the antigen into, say a rabbit. Then the second antibody can be induced by introducing serum or $\gamma$ globulin of a rabbit into, say, a donkey.

The colored protein can be any protein that does not interfere with the immunoassay and that can be precipitated independently of the antigen being assayed. Thus, the choice of protein will depend upon the particular assay. Typically, however, the protein will be a larger molecule than the antigen and, preferably, the protein will have an average molecular weight in excess of about 100,000. Bovine gamma globulin, for example, has been found quite suitable for use in this invention.

The protein can be colored by using any conventional protein colorant or dye. Examples of suitable dyes include, for instance, Alcian Blue, Coomassie Blue, Methylene Blue, Amido Black, Ponceau S., Methyl Green, Bromophenol Blue, Indigo Carmine, and Crystal Violet, etc.

A sufficient amount of dye is added to the protein so that the pellet obtained in the immunoassay will be colored for easy visualization. The amount for any particular embodiment will of course depend upon the amount of protein used in the assay and the amount of protein that is precipitated in the assay, among other things. Typically, an amount of dye in the range of from about 0.0001 to about 0.1% by weight based on the final assay mixture is used. Preferably, the amount of dye used is from about 0.001 to about 0.05% by weight.

One way to determine the optimum amount of dye to be used is to prepare a series of samples of colored protein at various concentrations of dye in a buffered solution containing the concentration of protein to be used in the assay, add the precipitating agent to 1 ml of the colored protein solution, and centrifuge or spin down to obtain a pellet. Decant the supernatant and redissolve the pellet in 1 ml of distilled water. Measure the optical density (O.D.) of the supernatant and the solution of redissolved pellet at a suitable wavelength of light. The optimum concentration for the particular dye is the concentration at which the largest difference in optical density is found between the supernatant and the solution of redissolved pellet. Preferably, the supernatant is essentially colorless.

The amount of protein can vary over a wide range as long as there is sufficient protein so that, when colored and a coprecipitate is formed, the pellet is capable of easy visualization. Quantities of protein greater than 0.1% by weight based on the final assay mixture have been found useful. Preferably, at least 0.5% by weight protein is used.

The colored protein can be prepared by making a liquid concentrate of a protein dye in an aqueous or aqueous compatible solution. The protein, for example, bovine $\gamma$ globulin, is first dissolved in a buffer solution. A 0.01 M phosphate buffer solution having a pH of 7.4 has proved suitable. Other buffer solutions can be substituted for convenience by those skilled in the art. The dye is added to the protein containing buffer solution and mixed for a suitable period of time, say about ten minutes, to obtain the colored protein. Other conventional additives such as, for example, sodium chloride and sodium azide can be added to the colored protein solution to facilitate storage and other properties.

The precipitating agent is used to precipitate the colored protein with the double antibody-antigen complex to form the colored pellet in accord with the present invention. Any agent that is useful for precipitating protein can be used as the precipitating agent of this invention providing it does not cause the antigen to precipitate. Examples of useful water soluble precipitating agents include polyethylene glycol, polylysine, dextran, polyvinylpyrrolidone, polyvinyl alcohol, and the like. For a description of some effects of such agents on proteins, see *Clinical and Biochemical Analysis*, Volume 7, "Automated Analysis", Part 1, edited by Robert F. Ritchie, Chapter 3 entitled "Enhancing Effects of Nonionic Polymers on Immunochemical Reactions" by Kristoffer Hellsing, pp. 67-112, which is hereby incorporated by reference. Polyethylene glycol is presently preferred as a precipitating agent, particularly polyethylene glycol having an average molecular weight of about 6000 or greater. It can be recognized by those skilled in the art that it is generally preferred to coprecipitate the colored protein and the double antibody-antigen complex, particularly to simplify the assay procedure.

The amount of precipitating agent used in any particular assay depends, among other things, upon the antigen being assayed, the colored protein used, the amount of colored protein used, the type of sample, etc. Typically, the precipitating agent is used in sufficient quantity to precipitate at least a sufficient portion of the colored protein to achieve the visibility desired without precipitating the antigen from the assay mixture. Generally, at least about 1½% by weight based on the volume of the total assay solution (all ingredients added) will be useful. Preferably, a concentration of from about 2.5% to about 4% of precipitating agent is used in the final assay mixture.

The precipitating agent may also aid in the precipitation of the antibody-antigen complex. See Ritchie, above; Harrington et al., "Polymer Induced Precipitation of Antigen-Antibody Complexes: 'Precipiplex' Reactions", *Immunochemistry*, Vol. 8, pp. 413-21 (1971); Creighton et al., "Detection of Antibodies and Soluble Antigen-Antibody Complexes by Precipitation with Polyethylene Glycol", *J. Immunology*, Vol. 111, No. 4, pp. 1219-27 (1973); and Desbuguois et al., "Use of Polyethylene Glycol to Separate Free and Antibody-Bound Peptide Hormones in Radioimmunoassays", *J. Clin. Endocr.*, 33, 732 (1971); which are hereby incorporated by reference.

In one embodiment of the invention, a kit is provided comprising (1) A mixture of a known amount of labelled version of the antigen to be assayed and colored protein, (2) a first antibody, for the antigen to be assayed and (3) a mixture of (a) a second antibody for the complex of the first antibody and the antigen and (b) a precipitating agent.

To perform an immunoassay using such a kit, a sample containing an unknown amount of the antigen to be assayed is mixed with the labelled antigen, colored protein and first antibody in a buffered solution. After mixing for sufficient time to effect an equilibrium, the second antibody and precipitating agent are added to the assay solution. The second antibody reacts with the first antibody-antigen complex to form an insoluble, but essentially invisible complex. At the same time the precipitating agent effects the coprecipitation of colored protein. After sufficient time for the reaction to be complete, the precipitate is spun down and colored pellet is formed. The supernatant can easily be removed and the pellet analyzed by known techniques to determine the amount of antigen present in the sample. Of course, the colored protein can be added at any time prior to the precipitating agent as long as it does not interfere with the binding of the antigen and antibodies to form a complex. In some instances it may be preferable to add the colored protein and precipitating agent after the complex is precipitated and thus precipitate the colored protein after the complex is formed.

In a preferred embodiment of the invention, prereacted first and second antibodies are used in place of separate first and second antibodies. In this case the kit preferably contains the prereacted first and second antibodies in mixture with the precipitating agent. Thus, when used to perform an immunoassay, all of the components are mixed together with the sample in one step.

The following examples are provided to further illustrate the invention. Unless otherwise indicated all percentages are based on weight.

EXAMPLE 1

A stock solution of colored protein is made by first dissolving 16 g of bovine $\gamma$-globulin in about 900 ml of 0.01 M $PO_4^{--}$ buffer at pH 7.4. Then 10 g of Alcian Blue is dissolved in 100 ml of a solution of methyl alcohol:water:glacial acetic acid that is mixed in a ratio of 5:5:1 respectively by volume. 1 ml of dye solution is added to the $\gamma$-globulin solution and mixed for about ten minutes. NaCl is added to the colored $\gamma$-globulin solution to give 0.9% NaCl keeping the pH adjusted to 7.4 and the total volume of solution is brought to 1 liter. Then 0.1% sodium azide is added to the colored $\gamma$-globulin stock solution. The final solution is filtered through a $0.45\mu$ filter to remove particulates.

EXAMPLE 2

Immunoassay for Gentamicin

A prereacted first and second antibody solution was made by diluting 10 $\mu$l of sheep anti-gentamicin (sheep antibody) and 2 ml of donkey anti-sheep antibody (antibody to the sheep $\gamma$-globulin) in 100 ml of 0.01 M phosphate buffer at pH 7.4 containing 0.1% gelatin, 0.9% NaCl and 0.1% sodium azide. After mixing for about 15 minutes, 6.4 g of polyethylene glycol having an average molecular weight of about 6000 (PEG 6K) is added. Approximately 500 pg of radioactive-labelled gentamicin is added to 0.5 ml of the colored $\gamma$-globulin solution of Example 1 to provide a predetermined quantity, about 50,000 counts per minute, of radioactivity. Then, samples of serum containing known or unknown quantities of gentamicin were diluted 1 part to 100 parts water and 0.05 ml of the diluted sample was added to the 0.5 ml of above solution containing labelled gentamicin and the colored protein. Next, 0.5 ml of the prereacted antibody solution was added to the colored $\gamma$-globulin solution containing the sample. The final assay mixture was mixed, allowed to stand at room temperature for about 10 minutes, and the resulting precipitate was centrifuged to obtain a blue colored pellet. The supernatants were easily decanted from the highly visible blue pellets and the pellets were analyzed for radioactivity. The radioactivity of the unknown was then compared with a curve generated with standards of different known amounts of gentamicin to determine the amount of gentamicin in the unknown serum.

EXAMPLE 3

Immunoassay for Tobramycin

A prereacted first and second antibody solution was made by dissolving 10 $\mu$l of sheep anti-tobramycin (sheep antibody) and a titred amount of donkey anti-sheep antibody (antibody to the sheep $\gamma$-globulin) in 100 ml of 0.01 M phosphate buffer at pH 7.4 containing 0.1% gelatin, 0.9% NaCl and 0.1% sodium azide. After mixing for about 15 minutes, 6.4 g of polyethylene glycol having an average molecular weight of about 6000 (PEG 6K) is added. Approximately 1000 pg of radioactive-labelled tobramycin is added to 0.5 ml of the colored $\gamma$-globulin solution of Example 1 to provide a predetermined quantity, about 50,000 counts per minute, of radioactivity. Then, a sample of serum containing an unknown quantity of tobramycin was diluted 1 part to 200 parts water and 0.05 ml of the diluted sample was added to the above solution containing labelled tobramycin and the colored protein. Next, 0.5 ml of the prereacted antibody solution was added to the colored $\gamma$-globulin solution containing the sample. The final assay mixture was allowed to stand at room temperature for about 10 minutes and the resulting precipitate was centrifuged to obtain a blue colored pellet. The supernatants were easily decanted from the highly visible blue pellet and the pellets were analyzed for radioactivity. The radioactivity of the unknowns were then compared with a curve generated with standards of different known amounts of tobramycin to determine the amount of tobramycin in the serum.

EXAMPLE 4

Immunoassay for Digoxin

A prereacted first and second antibody solution was made by dissolving 25 $\mu$l of diluted (1:1000) rabbit anti-digoxin (rabbit antibody) and a titred amount of sheep anti-rabbit antibody (antibody to the rabbit $\gamma$-globulin) in 100 ml of 0.01 M phosphate buffer at pH 7.4 containing 0.1% gelatin, 0.9% NaCl and 0.1% sodium azide and normal rabbit serum 1:4000. After mixing for about 15 minutes, 6.4 g of polyethylene glycol having an average molecular weight of about 6000 (PEG 6K) is added. A predetermined quantity of radioactive-labelled digoxin having approximately 50,000 counts per minute of radioactivity is added to 0.5 ml of the colored $\gamma$-globulin solution of Example 1. Then, 0.1 ml of samples of serum containing known and unknown quantities of digoxin were added to the 0.5 ml of above solution containing labelled digoxin and the colored protein. Next, 0.5 ml of the prereacted antibody solution was added to the colored $\gamma$-globulin solution containing the sample. The final assay mixture was mixed for about 30 minutes and the resulting precipitate was centrifuged to obtain a blue colored pellet. The supernatant was easily decanted from the highly visible blue pellet and the pellet was analyzed for radioactivity. The radioactivity was then compared with a curve generated with standards of different known amounts of digoxin to determine the amount of digoxin in the unknown serum.

EXAMPLE 5

A second stock solution of colored protein was made similar to Example 1 except that the buffer used was 0.1 M acetate buffer at pH 4.3 and the final solution contained 0.002% Alcian Blue and 0.05 M ethylenediaminetetraacetic acid (EDTA)

EXAMPLE 6

Immunoassay for Cortisol (Hydrocortisone)

A prereacted first and second antibody solution was made by dissolving 0.08 ml of rabbit anti-cortisol (rabbit antibody) and titred amount of sheep anti-rabbit antibody (antibody to the rabbit $\gamma$-globulin) in 100 ml of 0.01 M phosphate buffer at pH 7.4 containing 0.1% gelatin, 0.9% NaCl and 0.1% sodium azide. After mixing for about 15 minutes, 3.2 g of polyethylene glycol having an average molecular weight of about 6000 (PEG 6K) is added. Approximately 50,000 counts per minute of radioactive-labelled cortisol is added to 0.5 ml of the colored $\gamma$-globulin solution of Example 5 to provide a predetermined quantity of radioactivity. Then a 0.01 ml sample of serum containing an unknown quantity of cortisol was added to the above solution containing labelled cortisol and the colored protein. Next, 0.5 ml of the prereacted antibody solution was added to the colored $\gamma$-globulin solution containing the sample. The final assay mixture was mixed for about 30 minutes and the resulting precipitate was centrifuged to obtain a blue colored pellet. The supernatants were easily decanted from the highly visible blue pellet and the pellets were analyzed for radioactivity. The radioactivity was then compared with a curve generated with standards of different known amounts of cortisol to determine the amount of cortisol in the serum.

The present invention has been described in detail, including the preferred embodiments thereof. However, it will be appreciated that those skilled in the art may make modifications within the spirit and scope of the invention.

We claim:

1. A method for performing an immunoassay, said method comprising:
   reacting an antigen and a labelled version of said antigen with a first antibody for said antigen and said first antibody with a second antibody for said first antibody to precipitate a complex of said antigen, said first antibody and said second antibody, and
   precipitating a colored protein to form a precipitate comprised of said complex and colored protein.

2. The method of claim 1 wherein said precipitation of colored protein is effected by adding a precipitating agent in a sufficient amount to precipitate at least a portion of the colored protein to form a colored precipitate for easy visualization.

3. The method of claim 1 wherein said antigen is selected from the group consisting of gentamicin, tobramycin, theophylline, digoxin, and hydrocortisone.

4. The method of claim 1 wherein said colored protein is formed by mixing a protein and a protein dye in an aqueous solution.

5. The method of claim 3 wherein said protein has an average molecular weight of at least about 100,000.

6. The method of claim 3 wherein said dye is present in the range of about 0.0001 to 0.1% by weight of the final assay mixture.

7. The method of claim 3 wherein said protein is present in an amount of at least 0.1% by weight of the final assay mixture.

8. The method of claim 1 wherein said precipitating agent is selected from the group consisting of polyethylene glycol, polylysine, dextran, polyvinylpyrolidone and polyvinyl alcohol.

9. The method of claim 1 wherein said precipitating agent is polyethylene glycol having an average molecular weight of at least about 6000.

10. The method of claim 1 wherein said precipitating agent is present in an amount of at least about 1½% by weight of the final assay mixture.

11. The method of claim 1 wherein said labelled version of the antigen is radio-labelled.

12. A method for performing an immunoassay, said method comprising:
    mixing an aqueous mixture of (1) a sample containing an antigen to be assayed, (2) a known quantity of a labelled version of the antigen, and (3) a first antibody for the antigen in an amount insufficient to react with all the antigen, thus forming a first antibody-antigen complex; and
    adding to said aqueous mixture (4) a second antibody that reacts with the first antibody-antigen complex to form a precipitate, (5) a colored protein and (6) a precipitating agent that effects the precipitation of at least some of the colored protein; thus forming a colored precipitate for easy visualization.

13. The method of claim 12 wherein said antigen is selected from the group consisting of gentamicin, tobramycin, theophylline, digoxin and hydrocortisone.

14. The method of claim 12 wherein said colored protein is formed by mixing a protein and a protein dye in an aqueous solution.

15. The method of claim 14 wherein said protein has an average molecular weight of at least about 100,000.

16. The method of claim 14 wherein said dye is present in the range of about 0.0001 to 0.1% by weight of final assay mixture.

17. The method of claim 14 wherein said protein is present in an amount of at least 0.1% by weight of the final assay mixture.

18. The method of claim 12 wherein said precipitating agent is selected from the group consisting of polyethylene glycol, polylysine, dextran, polyvinylpyrolidone and polyvinyl alcohol.

19. The method of claim 12 wherein said precipitating agent is polyethylene glycol having an average molecular weight of at least about 6000.

20. The method of claim 12 wherein said precipitating agent is present in an amount of at least about 1½% by weight of the final assay mixture.

21. The method of claim 12 wherein said labelled version of the antigen is radio-labelled.

22. A method for performing an immunoassay, said method comprising incubating an aqueous mixture of (1) a sample containing an antigen to be assayed, (2) a known quantity of a labelled version of the antigen, (3) a prereacted first and second antibody for the antigen in an amount insufficient to react with all of the antigen, (4) a colored protein and (5) a precipitating agent that effects the precipitation of at least some of the colored protein, thus forming a colored precipitate for easy visualization.

23. The method of claim 22 wherein said antigen is selected from the group consisting of gentamicin, tobramycin, theophylline, digoxin, and hydrocortisone.

24. The method of claim 22 wherein said colored protein is formed by mixing a protein and a protein dye in an aqueous solution.

25. The method of claim 24 wherein said protein has an average molecular weight of at least about 100,000.

26. The method of claim 24 wherein said dye is present in the range of about 0.0001 to 0.1% by weight of the final assay mixture.

27. The method of claim 24 wherein said protein is present in an amount of at least 0.1% by weight of the final assay mixture.

28. The method of claim 22 wherein said precipitating agent is selected from the group consisting of polyethylene glycol, polylysine, dextran, polyvinylpyrolidone and polyvinyl alcohol.

29. The method of claim 22 wherein said precipitating agent is polyethylene glycol having an average molecular weight of at least about 6000.

30. The method of claim 22 wherein said precipitating agent is present in an amount of at least about $1\frac{1}{2}$% by weight of the final assay mixture.

31. The method of claim 22 wherein said labelled version of the antigen is radio-labelled.

32. A kit for performing the immunoassay for an antigen, said kit comprising, in combination:
1. a predetermined amount of a labelled version of the antigen to be assayed;
2. a predetermined amount of a first antibody to react with the antigen to be assayed to form a first antibody-antigen complex;
3. a predetermined amount of a second antibody to react with the first antibody-antigen complex to form a precipitate;
4. a predetermined amount of colored protein; and
5. a predetermined amount of a precipitating agent to effect the coprecipitation of at least some of the colored protein.

33. The immunoassay kit of claim 32 wherein said antigen is selected from the group consisting of gentamicin, tobramycin, theophylline, digoxin, and hydrocortisone.

34. The immunoassay kit of claim 32 wherein said colored protein is formed by mixing a protein and a protein dye in an aqueous solution.

35. The immunoassay kit of claim 34 wherein said protein has an average molecular weight of at least about 100,000.

36. The immunoassay kit of claim 34 wherein said dye is present in the range of about 0.0001 to 0.1% by weight of the final assay mixture.

37. The immunoassay kit of claim 34 wherein said protein is present in an amount of at least 0.1% by weight of the final assay mixture.

38. The immunoassay kit of claim 32 wherein said precipitating agent is selected from the group consisting of polyethylene glycol, polylysine, dextran, polyvinylpyrolidone and polyvinyl alcohol.

39. The immunoassay kit of claim 32 wherein said precipitating agent is polyethylene glycol having an average molecular weight of at least about 6000.

40. The immunoassay kit of claim 32 wherein said precipitating agent is present in an amount of at least about $1\frac{1}{2}$% by weight of the final assay mixture.

41. The immunoassay kit of claim 32 wherein said labelled version of the antigen is radio-labelled.

42. A kit for performing the immunoassay for an antigen, said kit comprising, in combination:
1. a predetermined amount of a labelled version of the antigen to be assayed;
2. a predetermined amount of a prereacted first and second antibody for said antigen;
3. a predetermined amount of colored protein; and
4. a predetermined amount of a precipitating agent to effect the coprecipitation of at least some of the colored protein.

43. The immunoassay kit of claim 42 wherein said antigen is selected from the group consisting of gentamicin, tobramycin, theophylline, digoxin, and hydrocortisone.

44. The immunoassay kit of claim 42 wherein said colored protein is formed by mixing a protein and a protein dye in an aqueous solution.

45. The immunoassay kit of claim 44 wherein said protein has an average molecular weight of at least about 100,000.

46. The immunoassay kit of claim 44 wherein said dye is present in the range of about 0.0001 to 0.1% by weight of the final assay mixture.

47. The immunoassay kit of claim 44 wherein said protein is present in an amount of at least 0.1% by weight of the final assay mixture.

48. The immunoassay kit of claim 42 wherein said precipitating agent is selected from the group consisting of polyethylene glycol, polylysine, dextran, polyvinylpyrolidone and polyvinyl alcohol.

49. The immunoassay kit of claim 42 wherein said precipitating agent is polyethylene glycol having an average molecular weight of at least about 6000.

50. The immunoassay kit of claim 42 wherein said precipitating agent is present in an amount of at least about $1\frac{1}{2}$% by weight of the final assay mixture.

51. The immunoassay kit of claim 42 wherein said labelled version of the antigen is radio-labelled.

52. The precipitate comprising in admixture a colored protein and a complex of an antigen, a first antibody for said antigen and a second antibody for said first antibody, wherein at least a portion of said antigen is labelled.

* * * * *